(12) United States Patent
Matsubara et al.

(10) Patent No.: US 7,754,255 B2
(45) Date of Patent: Jul. 13, 2010

(54) BONE METABOLISM IMPROVING AGENT

(75) Inventors: Satoshi Matsubara, Tokyo (JP); Hiroko Hayakawa, Tokyo (JP); Yasuhisa Shimakawa, Tokyo (JP); Mitsuyoshi Kano, Tokyo (JP); Harue Sone, Tokyo (JP); Fumiyasu Ishikawa, Tokyo (JP)

(73) Assignee: Kabushiki Kaisha Yakult Honsha, Tokyo (JP)

( * ) Notice: Subject to any disclaimer, the term of this patent is extended or adjusted under 35 U.S.C. 154(b) by 0 days.

(21) Appl. No.: 11/768,524

(22) Filed: Jun. 26, 2007

(65) Prior Publication Data

US 2007/0298146 A1 Dec. 27, 2007

Related U.S. Application Data

(62) Division of application No. 10/398,507, filed as application No. PCT/JP01/08486 on Sep. 28, 2001.

(30) Foreign Application Priority Data

Oct. 13, 2000 (JP) ............... 2000-313223

(51) Int. Cl.
- A23G 1/02 (2006.01)
- A23L 1/20 (2006.01)
- A23F 3/00 (2006.01)
- A23C 9/12 (2006.01)
- A61K 47/00 (2006.01)

(52) U.S. Cl. ............... 426/44; 426/34; 426/46; 426/49; 424/439

(58) Field of Classification Search ............... None
See application file for complete search history.

(56) References Cited

FOREIGN PATENT DOCUMENTS

| EP | 1 010 753 A1 | 6/2000 |
|----|----|----|
| JP | 5-176718 | 7/1993 |
| JP | 5-268907 | 10/1993 |
| JP | 6-46797 | 2/1994 |
| JP | 7-75525 | 3/1995 |
| JP | 7-284383 | 10/1995 |
| JP | 9-191852 | 7/1997 |
| JP | 9-238647 | 9/1997 |
| JP | 10-56959 | 3/1998 |
| JP | 10-114653 | 5/1998 |
| JP | 10-130160 | 5/1998 |
| JP | 11-12172 | 1/1999 |
| JP | 11-346716 | 12/1999 |
| JP | 2000-14356 | 1/2000 |
| JP | 2000-53573 | 2/2000 |
| JP | 2000-139411 | 5/2000 |
| JP | 2000212079 A * | 8/2000 |

OTHER PUBLICATIONS

English translation of Ishikawa et al. JP 09238647 A, pp. 1-17, Sep. 16, 1997.*
Yazici et al. J. Food Science. 62(3):. 457-461, 1994.
Sugimoto et al. J. Food Processing and Preservation. 5(2): 83-93, 1981.
Kikuchi-Hayakawa et al. Biosc. Biotechnol. Biochem. 62: 1688-1692, 1998.
Yamaguchi et al. J. Bone Miner. Metab. 17: 23-29, 1999.
Potter et al. Am. J. Nutr. 68: 6 Suppl. 1375S-1379S, 1998.
Blair et al. J. Cell Bioche. 61: 629-637, 1996.
Ishikawa et al. Gastroenterology 118, Supple. 2L A 779, #4171, Apr. 2000.
Arjmandi et al. J. Nutrition 126: 161-167, 1996.
Spanhaak et al. Eur. J. Clin. Nutrition 52: 899-907, 1998.
Kikuchi-Hayakawa et al. J. Nutr. Sci. Vitaminol. 46: 105-108, Apr. 2000.
Omi et al. J. Nutri. Sci. Vitaminol. 40: 201-211, 1994.

* cited by examiner

*Primary Examiner*—S. Devi
(74) *Attorney, Agent, or Firm*—Oblon, Spivak, McClelland, Maier & Neustadt, L.L.P.

(57) ABSTRACT

A bone metabolism improving agent characterized by containing as the active ingredient fermented soybean milk which is obtained by fermenting soybean milk with a lactic acid bacterium or a bifidobacterium. The bone metabolism improving agent is efficacious in treating and preventing diseases in association with lowered bone metabolism such as osteoporosis and, at the same time, satisfies requirements in cost and smooth intake.

7 Claims, 4 Drawing Sheets

BONE METABOLISM IMPROVING AGENT

This application is a divisional of co-pending U.S. patent application Ser. No. 10/398,507, filed Apr. 11, 2003, which is a national stage application of PCT/JP01/08486, filed Sep. 28, 2001, which claims benefit of the filing date of the Japanese application 2000-313223, filed Oct. 13, 2000.

FIELD OF THE INVENTION

The present invention relates to a bone metabolism improving agent, and more particularly to a bone metabolism improving agent comprising fermented soy milk that is efficacious in treating and preventing diseases associated with a decrease in bone metabolism such as osteoporosis.

DESCRIPTION OF BACKGROUND ART

Women are highly susceptible to diseases associated with an unbalance in bone metabolism such as osteoporosis, particularly after menopause when female hormones decrease. People affected with osteoporosis are highly susceptible to bone fractures due to the low density of their bones. Elderly people, in particular, can become bedridden due to these bone fractures. Prevention of these problems has been strongly demanded.

Since raising bone density by improving the bone metabolism is desirable for such people having a tendency toward a decrease in bone density, there are some reported technologies with an object of improving bone metabolism. For example, the calcium absorption promotion effect of soy milk and the calcium absorption promotion substance in soy milk have been reported in Japanese Patent Application Laid-open Nos. 1994-46797 and 1995-75525, and the like. However, a satisfactory effect has not yet been achieved.

It has also been reported that isoflavone and a composition consisting of isoflavone and zinc or a peptide increase bone metabolism (Japanese Patent Application Laid-open Nos. 1998-114653 and 2000-139411). However, obtaining these components requires a complicated process. Although the isoflavone or the composition may be used as a medicine, it is difficult to say that the isoflavone or composition is suitable for use in applications to be taken continuously during routine life for improving bone metabolism.

At present, a method for improving bone metabolism satisfying all the characteristics of efficacy, economy, and ease of ingestion is not provided. An object of the present invention is to provide such a method.

DISCLOSURE OF THE INVENTION

As a result of extensive studies to achieve the above object, the present inventors have found that if soy milk which has already been known to have a calcium absorption improving effect is fermented, the bone metabolism improving effect rapidly increases. This finding has led to the completion of the present invention.

Specifically, the present invention provides a bone metabolism improving agent comprising fermented soy milk as an active ingredient which is obtained by fermenting soy milk with one or more microorganisms selected from the group consisting of *Lactobacillus casei, Lactobacillus mali*, and *Bifidobacterium breve*.

The present invention further provides a method for improving bone metabolism in humans and animals comprising administering an absorbent comprising a bone metabolism improving agent containing fermented soy milk as an active ingredient which is obtained by fermenting soy milk with one or more microorganisms selected from the group consisting of *Lactobacillus casei, Lactobacillus mali*, and *Bifidobacterium breve* to humans and animals.

DETAILED DESCRIPTION OF THE INVENTION AND PREFERRED EMBODIMENT

Figure 1:
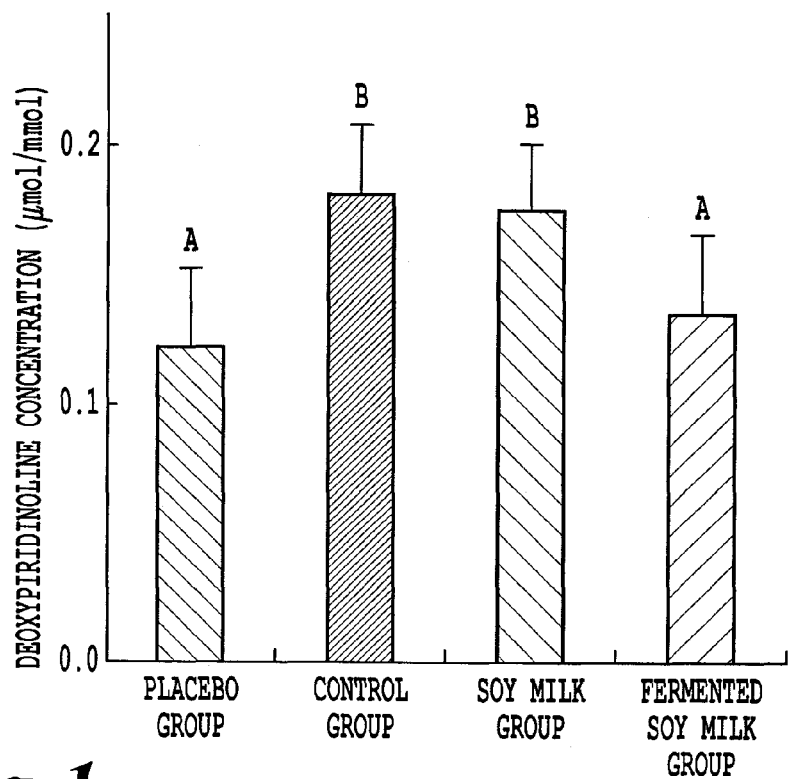
FIG. 1 shows the results of measurement of deoxypyridinoline discharged in urine.

The bone metabolism improving agent of the present invention controls bone absorption, and as a result, increases bone density and mineral content in bone. The fermented soy milk used as the active ingredient in the bone metabolism improving agent of the present invention is prepared by inoculating one or more microorganisms selected from the group consisting of *Lactobacillus casei, Lactobacillus mali*, and *Bifidobacterium breve* in soy milk and causing the soy milk to ferment. The soy milk used as the raw material for the fermented soy milk can be produced by any method as long as the soybean component is suspended or dissolved in a liquid. As examples, whole soybeans or defatted soybeans soaked in water or hydrated, ground into slurry, and filtered to remove insoluble components, and soybean protein dissolved or suspended in water can be given.

As examples of the lactic acid bacterium and bifidobacterium used in the production of the fermented soy milk used as the active ingredient in the bone metabolism improving agent of the present invention, *Lactobacillus* bacteria such as *L. acidphilus, L. gasseri, L. mali, L. plantarum, L. pentosus, L. buchneri, L. casei, L. johnsonii, L. gallinarum, L. amylovorus, L. brevis, L. rhamnosus, L. kefir, L. paracasei, L. crispatus, L. bulgaricus, L. fermentum, L. reuteri, L. alimentarius*, and *L. maltaromicus; Streptococcus* bacteria such as *S. thermophilus; Lactococcus* bacteria such as *L. lactis* and *L. cremoris; Leuconostoc* bacteria such as *L. cremoris; Bifidobacterium* bacteria such as *B. bifidum, B. longum, B.*

Of these, *L. casei, L. mali, B. breve, L. plantarum, L. rhamnosus, L. paracasei, L. crispatus, L. lactis, B. adolescentis*, and *B. pseudocatenulatum*, singularly or in a combination of two or more, are preferable due to the increased bone metabolism improving effect and good taste of the fermented soy milk. *L. casei, L. mali*, and *B. breve* are particularly preferable. As specific examples of these bacteria, *L. casei* YIT9029 strain (FERM BP-1366), YIT0078 strain (ATCC393), and YIT0123 strain (ATCC27216), *L. mali* YIT0243 strain (ATCC27304), *B. breve* YIT4065 strain (FERM BP-6223), YIT4014 strain (ATCC15700), and YIT4063 strain (FERM BP-2823), *L. plantarum* YIT0103 strain (ATCC10241), *L. rhamnosus* YIT105 strain (ATCC7469), *L. paracasei* YIT0209 strain (ATCC25302), *L. crispatus* YIT0212 strain (ATCC33820), *L. lactis* YIT2027 strain (FERM P-16074), *B. adolescentis* YIT4011 strain (ATCC15703), *B. pseudocatenulatum* YIT4072 strain (ATCC27919), and the like can be given.

In addition, other microorganisms may be combined with the above lactic acid bacterium and *bifidobacterium* to produce the fermented soy milk of the present invention, for example, *Bacillus* bacteria such as *B. subtilis*, *Acetobacter* bacteria such as *A. aceti* and *A. xylinum*, and yeasts belonging to the *Saccharomyces*, *Torulaspora*, and *Candida* groups such as *S. cerevisiae*, *S. unisporus*, *K. marxianus*, *T. delbrueckii*, and *C. kefyr*.

The fermented soy milk used in the present invention can be produced using conventional methods. For example, after pasteurization, the soy milk is inoculated with the above lactic acid bacterium and *bifidobacterium* and cultured, then homogenized to produce fermented soy milk. The culturing conditions for fermenting the soy milk may be suitably selected. For example, if the bacteria are anaerobic, oxygen in the culture medium can be substituted with an inert gas such as carbon dioxide gas or nitrogen gas, or oxygen in the culture medium can be removed using an oxygen reaction agent to provide anaerobic conditions before culturing the bacteria. If the bacteria are aerobic, aerobic conditions may be selected for culturing.

Other conditions should be appropriately set in accordance with the type of microorganism used. For example, when a lactic acid bacterium or *bifidobacterium* is used, culturing may be conducted at 25° C.-37° C. for about 15-48 hours, and using soy milk at a concentration of 1-20% on a solid basis is preferable from the viewpoint of ensuring the bone metabolism improving effect of the fermented soy milk.

Various saccharides, nutrients, and components, for example, carbohydrates such as glucose, sucrose, fructose-glucose syrup, and glucose-fructose syrup, nutrients such as meat extract, yeast extract, peptide, and minerals, plant components such as grains, grain seed sprouts, vegetables, fruits, nuts, and herbs, animal components, and microorganism incubation components may be added to the soy milk used as a raw material in an amount of 0.01-99 mass %.

The bone metabolism improving agent of the present invention is prepared by providing the fermented soy milk obtained above in a proper form such as a medicine or food and in a proper state such as liquid, paste, or solid. The fermented soy milk can be used as is, concentrated to a certain degree, or freeze-dried to form a solid powder. In order to achieve the objective effect from the bone metabolism improving agent of the present invention, fermented soy milk having a soybean solid component content of 6% is ingested in an amount of 10-1,000 g a day per person, and preferably 100-300 g a day per person.

When using the bone metabolism improving agent of the present invention in a method for improving the bone metabolism of humans and animals, the above amounts are administered to humans and animals.

When the bone metabolism improving agent is used in the form of a food, various additives may be added and combined to improve the taste and to provide a desired shape, for example. In addition, a flavoring agent may be added.

As the additives to be added to and combined with the bone metabolism improving agent of the present invention, various carbohydrates, emulsifying agents, thickeners, sweeteners, sour additives, fruit juices, and the like can be given. As specific examples of these additives, saccharides such as glucose, sucrose, fructose, tagatose, trehalose, trehalulose, lactulose, xylooligosaccharide, isomaltoligosaccharide, lactose, galactooligosaccharide, fructooligosaccharide, raffinose, stachyose, glucosamine, inulin, honey, maple syrup, and amazake, sugar alcohols such as sorbitol, xylytol, erythritol, lactitol, and palatinit, high intensity sweeteners such as sucralose and aspartame, natural sweeteners such as liquorice, stevia, and glycyrrhizin acid glycoside, emulsifying agents such as sucrose fatty-acid ester, glycerol sugar fatty-acid ester, and lecitin, and thickeners (stabilizers) such as agar, gelatin, carageenan, guar gum, xanthan gum, pectin, and locust bean gum can be given. In addition, minerals such as calcium, magnesium, zinc, iron, and dolomite, acids such as citric acid, malic acid, ascorbic acid, lactic acid, acetic acid, and amino acid, filling materials such as collagen, chondroitin sulfate, hydroxyproline, flavone, flavonol, isoflavone, anthocyan, catechin, and proanthocyanidin, vitamins such as vitamin A, vitamin B group, vitamin C, vitamin E, vitamin D group, vitamin K group, beta carotene, retinoic acid, and folic acid, herb extracts such as black cohosh, soybeans, butternut seeds, pomegranate seeds, St. John's wort, passion flower, valerian, pueraria mirifica, rosemary, peppermint, lemon balm, and marigold, grains and grain seed sprouts such as rice, wheat, barley, rye, oat, and corn, vegetables such as potato, sweet potato, purple-fleshed sweet potato, yam, pumpkin, eggplant, tomato, bitter melon, green pepper, sesame seed, cabbage, broccoli, cauliflower, lettuce, red bean, broad bean, soybean, green soybean, green pea, ginger, burdock, celery, Japanese radish, Japanese horseradish, avocado, carrot, spinach, onion, garlic, lily, shallot, beefsteak plant (*Perilla frutescens*), leek, parsnip, bracken, bamboo shoot, shiitake mushroom, and mushroom, fruits such as lemon, apple, grape, strawberry, orange, persimmon, guava, banana, blueberry, pineapple guava, tree tomato, acerola, lime, hirami lemon, melon, peach, mango, yuzu orange, papaya, pineapple, pear, plum, grapefruit, Chinese quince, apricot, watermelon, pomegranate, kiwi, and mandarin orange, nuts such as peanut, almond, coconut, cashew, macadamia, cacao, chestnut, ginkgo, and walnut, dairy products such as milk, defatted milk, whey, cream, fermented milk, and yogurt may be added to obtain a delicious flavor.

In addition, as flavoring agents that may be added to the bone metabolism improving agent of the present invention, yogurt, berry, orange, Chinese quince, beefsteak plant (*Perilla frutescens*), citrus, apple, mint, grape, pear, custard cream, peach, melon, banana, tropical, herb, tea, coffee, and the like can be given. These flavoring agents may be used singularly or in a combination of two or more.

As containers for the bone metabolism improving agent of the present invention obtained in this manner, hermetic containers having low or high oxygen permeability can be given. Furthermore, the inside of these hermetic containers may be substituted with an inert gas.

EXAMPLES

The present invention will be described in more detail by examples, which should not be construed as limiting the present invention.

Example 1

Production of Soy Milk Feed and Fermented Soy Milk Feed (1):

(1) Production of Soy Milk Powder and Fermented Soy Milk Powder 20 liters of base soy milk (manufactured by Shikoku Kakoki Co., Ltd., containing 0.8% of glucose-fructose syrup) was sterilized in a plate sterilizer at 135° C. for 3.5 seconds. 10 liters of the sterilized soy milk was preserved at 4° C. The remaining 10 liters was inoculated with a bacteria solution containing 0.01% of *L. casei* YIT 9029 and 1% of *L. mali* YIT 0243, then cultured at 30° C. for 24 hours to obtain fermented soy milk. The preserved soy milk and the fermented soy milk were respectively freeze-dried and crushed to obtain soy milk and fermented soy milk powders.

(2) Feed Preparation

The following examination was conducted using feeds prepared from the components of Table 1. An AIN-93G composition, partly changed to be a low calcium feed with a calcium content of 0.1%, was used as a control feed. 4% each of soy milk powder and fermented soy milk powder were mixed to form a soy milk feed and a fermented soy milk feed. The mineral contents of the soy milk and the fermented soy milk powders were analyzed and three types of feed having an equal amount of calcium, phosphorus, and magnesium were produced.

TABLE 1

|  | Control feed | Soy milk feed | Fermented soy milk feed |
| --- | --- | --- | --- |
| Soy milk powder | — | 4.00 | — |
| Fermented soy milk powder | — | — | 4.00 |
| Casein | 20.00 | 18.36 | 18.36 |
| Soybean oil | 7.00 | 5.84 | 5.80 |
| Cellulose powder | 5.00 | 5.00 | 5.00 |
| Cornstarch | 39.75 | 39.75 | 39.75 |
| Dextrinized cornstarch | 13.20 | 13.20 | 13.20 |
| Sucrose | 9.05 | 7.93 | 7.97 |
| Choline tartrate | 0.25 | 0.25 | 0.25 |
| L-cysteine | 0.30 | 0.30 | 0.30 |
| Vitamin mixture | 1.00 | 1.00 | 1.00 |
| Ca, P, and Mg free mineral mixture | 3.50 | 3.50 | 3.50 |
| $CaCO_3$ | 0.23 | 0.21 | 0.21 |
| $KH_2PO_4$ | 0.64 | 0.60 | 0.60 |
| MgO | 0.08 | 0.06 | 0.06 |

Values indicate weight %

Example 2

Bone Metabolism Improvability Test (1):

36 eight-week-old SD-type rats (female) were purchased, an ovariectomy was conducted on both ovaries of 27 rats, and a placebo surgery was conducted on the remaining 9 rats. After administering the control feed for a two week recovery period, the ovariectomized rats were split into three groups (n=9): the ovariectomized-control feed group (hereinafter referred to as "control group"); the ovariectomized-soy milk feed group (hereinafter referred to as "soy milk group"); and the ovariectomized-fermented soy milk group (hereinafter referred to as "fermented soy milk group"). The rats that underwent placebo surgery are designated as the placebo surgery group.

For a period of 8 weeks, the placebo surgery and control feed groups were given control feed, the soy milk group was given soy milk feed, and the fermented soy milk group was given fermented soy milk feed. Animals were fed by pair feeding so that the feed intake of each group was almost equal and allowed to freely take ion-exchanged water. On the 8th week, urine was collected for 24 hours using a metabolic cage. After measuring the volume, the urine was stored at −20° C. until analysis. Vaginal mucous membrane epithelial cells were extracted for six days starting one week before dissection to observe the existence of keratosis cells, whereby it was confirmed that the placebo surgery group was sexually excited and the other groups were not sexually excited.

Under Nembutal anesthesia, the rats were slaughtered by draining the blood from the abdominal aorta, dissected, and the womb, femur, and tibia were removed. The bone density of the tibia and femur was determined by measuring the mass and volume after drying at 100° C. for 24 hours. Then, the tibia and femur were burnt to ash at 550° C. for 24 hours and the mass was measured. The mass per volume is indicated as the mineral content in the bone. For statistics processing, multiple comparison using Tukey's method was conducted after variance analysis (As shown in the drawing, there is a significant difference among the groups that do not possess the same letter (P<0.05)).

(Results)

Figure 2:
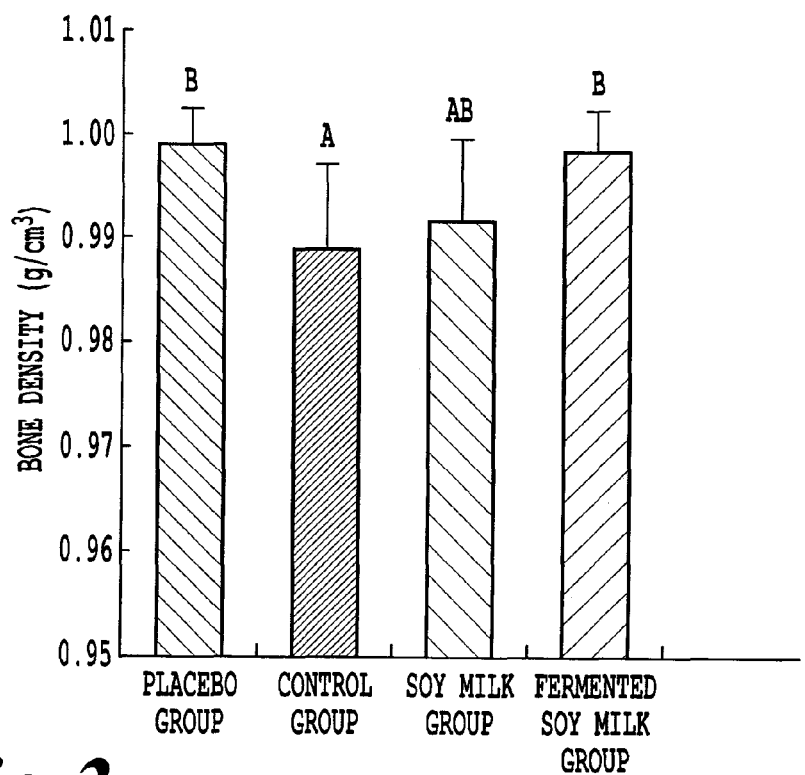
FIG. 2 shows the results of measuring bone density of the tibia.
Figure 3:
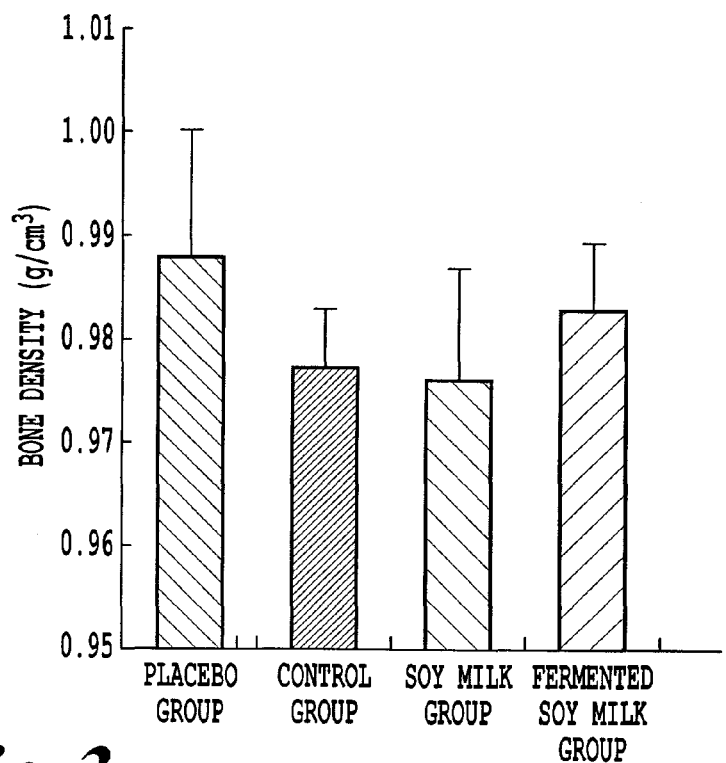
FIG. 3 shows the results of measuring bone density of the femur.
Figure 4:
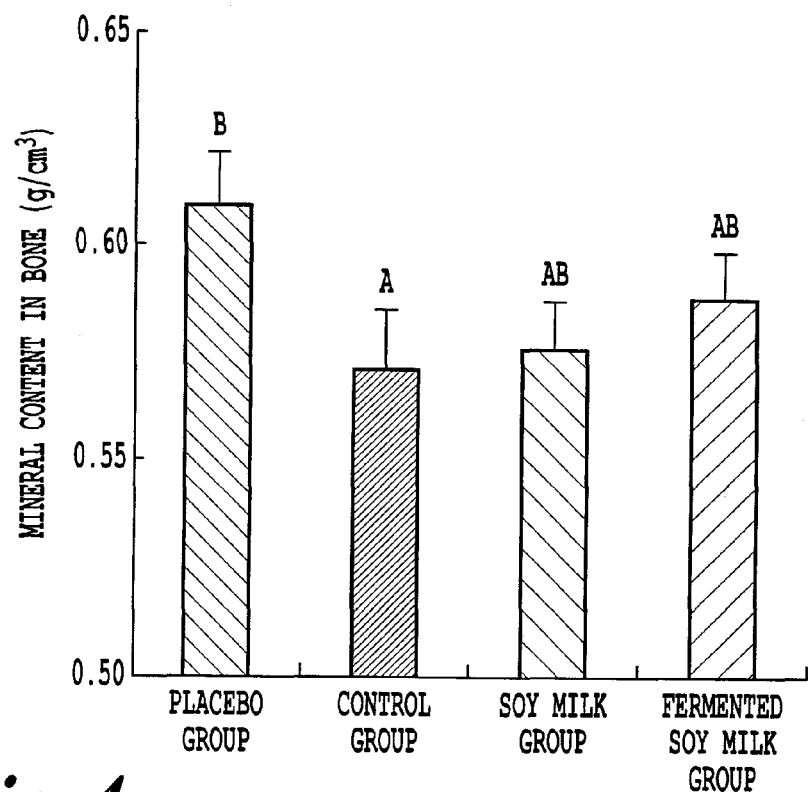
FIG. 4 shows the results of measuring mineral content in the tibia.
Figure 5:
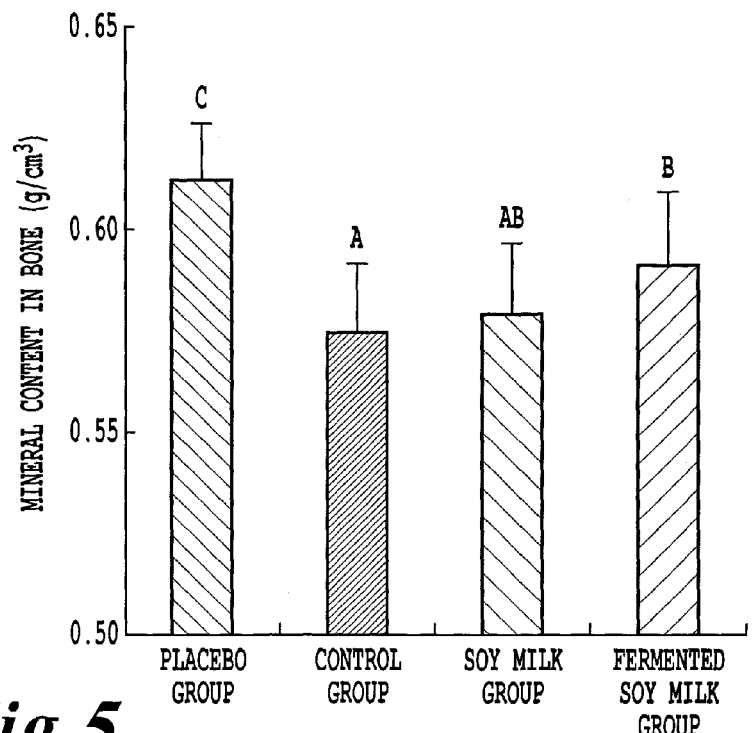
FIG. 5 shows the results of measuring mineral content in the femur.

The results of measuring deoxypyridinoline discharged in urine, which indicates the degree of bone resorption, are shown in FIG. 1. The results of measuring bone density of the tibia and femur are shown in FIGS. 2 and 3, respectively, and the results of measuring the mineral content in the bone are shown in FIGS. 4 and 5, respectively. The amount of deoxypyridinoline was measured using a clinical examination kit (Pyrilinks-D, manufactured by Mettler-Toledo International, Inc.) and the concentration per unit amount of creatinine measured beforehand using a Creatinine B tester (manufactured by Wako Pure Chemical Industries, Ltd.) is indicated. Deoxypyridinoline is the substance for crosslinking collagen and mainly exists in the bone. This substance is known as an excellent bone resorption indicator because the substance is released in response to bone resorption, discharged in urine without being metabolized, not absorbed by the alimentary canal, and not influenced by diet. It has been reported that deoxypyridinoline has a significant negative correlation with bone reduction rate (Fledelius C. et al., Calcif. Tissue Int. 54, 381-384, 1994).

It is clear from these results that the fermented soy milk group has a significantly low concentration of the bone metabolism indicator deoxypyridinoline in urine as compared with the control group and soy milk group, and this concentration is close to that of the placebo surgery group. Also, reduction in bone density and bone mineral content of the fermented soy milk group is less than that of the control group and soy milk group, and tibia bone density and femur mineral content is significantly higher than that of the control group. On the other hand, although the womb mass decreased to 11% due to ovariectomy, there was no significant difference on the womb mass among the control group, soy milk group, and fermented soy milk group.

Example 3

Preparation of Fermented Soy Milk Feed (2):

(1) Preparation of Soy Milk Powder and Fermented Soy Milk Powder 170 liters of base soy milk (manufactured by Shikoku Kakoki Co., Ltd.) was steam-sterilized at 100° C. for 90 minutes. 80 liters of the sterilized soy milk was preserved at 4° C. The remaining 90 liters was inoculated with a bacteria solution containing 1% of *Bifidobacterium breve* YIT 4065, then cultured at 34° C. for 15 hours to obtain fermented soy milk. The preserved soy milk and the fermented soy milk were freeze-dried and crushed to obtain soy milk and fermented soy milk powders.

(2) Preparation of Feed

An AIN-76 composition, partly changed to be a preparation feed with a protein content of 25% and a fat content of 17%, was used as a control feed. Soy milk and fermented soy milk feeds respectively containing 30% of soy milk powder and 30% fermented soy milk powder, (both powders containing 48% of crude protein and 24.3% of crude fat), were prepared by adding casein, corn oil, $CaCO_3$, $KH_2PO_4$, MgO, and sucrose to make the content of crude protein, crude fat, calcium, phosphorus, and magnesium equal to that of the control feed.

Example 4

Bone Metabolism Improvability Test (2):

24 eight-month-old parous Wistar rats (female), ovariectomized and confirmed not to be sexually excited, were split into three groups (n=8): control group, soy milk group, and fermented soy milk group. Also, a placebo surgery group was provided by conducting placebo surgery on eight rats of the same type and confirming the presence of sexual excitement.

The placebo surgery and control feed groups were given control feed, the soy milk group was given soy milk feed, and the fermented soy milk group was given fermented soy milk feed for 12 weeks. The rats were allowed to freely drink ion-exchanged water. The rats were not given food for four hours, anesthetized with Nembutal, slaughtered by draining the blood from the abdominal aorta, and dissected. The womb, femur, and tibia were removed. The bone density of the tibia was measured in the same manner as Example 2. To measure the calcium content of the femur, the femur was freeze-dried and burnt to ash at 550° C. for five hours. Wet ash obtained by adding nitric acid and perchloric acid to the ash was analyzed using a Sequential Plasma Spectrometer ICP-S2000 (manufactured by Shimadzu Corporation).

(Results)

Figure 6:
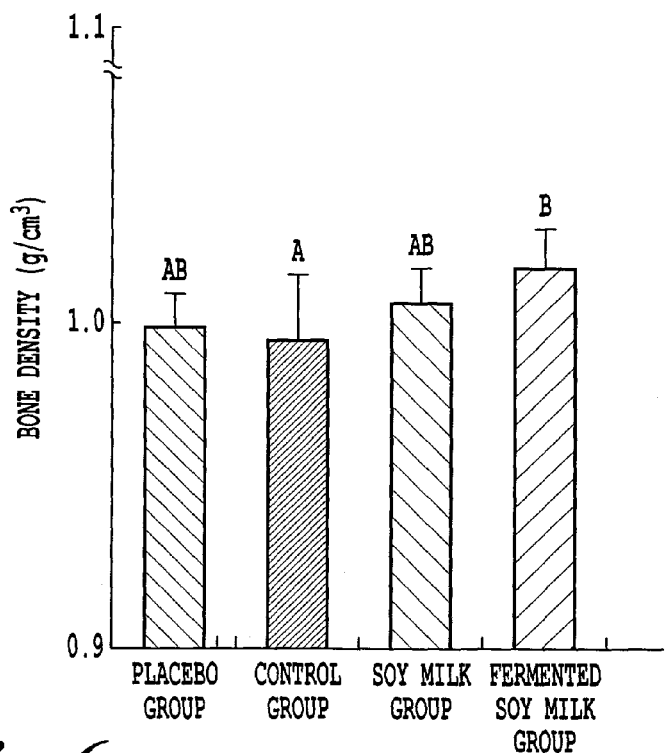
FIG. 6 shows the results of measuring bone density of the tibia.
Figure 7:
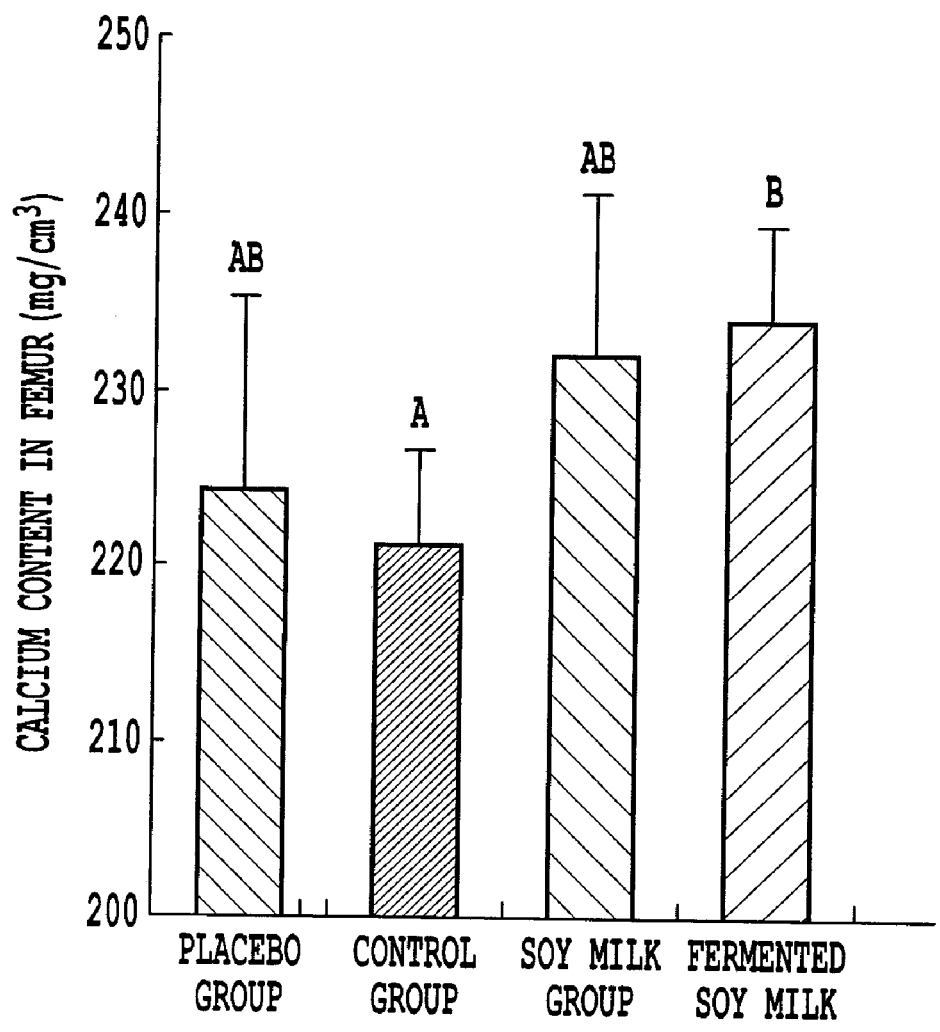
FIG. 7 shows the results of measurement of calcium content in the femur.

The results of measuring the bone density of the tibia are shown in FIG. 6, and the results of measuring the calcium content of the femur are shown in FIG. 7. The calcium content per dry mass and calcium content per volume of the femur for the fermented soy milk group were significantly higher than those of the control group. The calcium content for the soy milk group was the same as the control group. Also, the bone density and calcium content per volume of the tibia for the fermented soy milk group were significantly higher than those of the control group. The soy milk group displayed the same values as the control group. Furthermore, there was no difference in womb mass among the three ovariectomized groups, and there was no significant difference in initial weight, final weight, and feed intake.

It is clear from the above results that as compared with non-fermented soy milk, fermented soy milk is effective in preventing a decrease in the bone density resulting from an ovariectomy surgery. This shows that when non-fermented soy milk does not improve bone metabolism, fermented soy milk prepared from *Bifidobacterium breve* YIT4065 is effective in improving bone metabolism.

INDUSTRIAL APPLICABILITY

The above experiments show that fermented soy milk used as a bone metabolism improving agent is useful for women after menopause when the ability to synthesize and secrete female hormones is decreased. The fermented soy milk is also useful as a food for preventing harm to bone metabolism due to female hormone disorders that happen before menopause. Furthermore, it is clear from the above experiments that the fermented soy milk has a superior effect on bone metabolism as compared with soy milk.

Therefore, the bone metabolism improving agent of the present invention is very effective in treating and preventing diseases that accompany a decline in bone metabolism such as osteoporosis.

The invention claimed is:

1. A bone metabolism improving agent comprising fermented soy milk, which has been fermented by at least *Lactobacillus casei* and *Lactobacillus mali*.

2. The bone metabolism improving agent of claim 1, which increases (i) bone density and (ii) the mineral content of bone when administered to a human.

3. The bone metabolism improving agent of claim 1, which has been supplemented with at least one component selected from the group consisting of calcium, magnesium, iron and zinc.

4. The bone metabolism improving agent of claim 1, which has been supplemented with a vitamin.

5. The bone metabolism improving agent of claim 1, which has been supplemented with at least one of collagen, chondroitin sulfate, hydroxyproline, flavone, flavonol, isoflavone, anthocyan, catechin or proanthocyanidin.

6. The bone metabolism improving agent of claim 1, wherein the *Lactobacillus mali* is *Lactobacillus mali* strain YIT0243.

7. The bone metabolism improving agent of claim 1, wherein the *Lactobacillus casei* is *Lactobacillus casei* strain YIT9029.

* * * * *